United States Patent
Ma

(10) Patent No.: US 12,345,698 B2
(45) Date of Patent: Jul. 1, 2025

(54) METHOD FOR AUTHENTICATION OF ANIMAL SPECIES ORIGIN OF LEATHER PRODUCTS

(71) Applicant: Chinese Academy of Inspection and Quarantine, Beijing (CN)

(72) Inventor: Qiang Ma, Beijing (CN)

(73) Assignee: CHINESE ACADEMY OF INSPECTION AND QUARANTINE, Beijing (CN)

(*) Notice: Subject to any disclaimer, the term of this patent is extended or adjusted under 35 U.S.C. 154(b) by 816 days.

(21) Appl. No.: 17/666,700

(22) Filed: Feb. 8, 2022

(65) Prior Publication Data

US 2022/0229040 A1 Jul. 21, 2022

Related U.S. Application Data

(63) Continuation of application No. PCT/CN2021/070261, filed on Jan. 5, 2021.

(30) Foreign Application Priority Data

Jan. 6, 2020 (CN) .......................... 202010009806.2

(51) Int. Cl.
*G01N 33/44* (2006.01)
*H01J 49/40* (2006.01)
(Continued)

(52) U.S. Cl.
CPC ............ *G01N 33/447* (2013.01); *H01J 49/40* (2013.01); *H01J 49/429* (2013.01); *G01N 1/04* (2013.01); *G06F 2218/18* (2023.01)

(58) Field of Classification Search
USPC ....................................................... 250/288
See application file for complete search history.

(56) References Cited

U.S. PATENT DOCUMENTS

2016/0109349 A1 4/2016 Volckens et al.
2018/0047551 A1* 2/2018 Jones ..................... A61B 18/20
(Continued)

FOREIGN PATENT DOCUMENTS

CN 107646089 A 1/2018
CN 108700590 A 10/2018
(Continued)

OTHER PUBLICATIONS

Ling-Yun Yu et al., Study on Identification of Leather, Leather and Chemicals, vol. 33, No. 5, 2016.
(Continued)

*Primary Examiner* — Kiet T Nguyen
(74) *Attorney, Agent, or Firm* — troutman pepper locke; Tim Tingkang Xia, Esq.

(57) ABSTRACT

The present invention discloses a method for authentication of animal species origin of leather products, which includes the following steps: Step 1: Model establishment: (1) Collect leather samples from different animal species origins, set mass spectrometric parameters, cut the surface of leather samples using a preheated electric soldering iron, and detect the resulting sample ions using the mass spectrometer; (2) Create a multivariate statistical model based on principal component analysis and linear discriminant analysis of rapid evaporative ionization mass spectrometric data and evaluate the model with cross-validation tests; Step 2: Analysis of real leather samples: detect and authenticate the identity of real leather samples based on the multivariate statistical model. The authentication method disclosed in present invention is a rapid analytical method that requires no sample pretreatment and can identify the animal species origin of leather products rapidly and accurately.

5 Claims, 10 Drawing Sheets

(51) Int. Cl.
*H01J 49/42* (2006.01)
*G01N 1/04* (2006.01)

(56) References Cited

U.S. PATENT DOCUMENTS

2018/0047553 A1* 2/2018 Richardson ............ A61B 1/041
2018/0047554 A1* 2/2018 Takats ................. A61B 18/042

FOREIGN PATENT DOCUMENTS

| CN | 108828051 A | 11/2018 |
| CN | 110514732 A | 11/2019 |
| CN | 110596283 A | 12/2019 |
| CN | 111122690 A | 5/2020 |

OTHER PUBLICATIONS

Hong Lin, Identification of genuine leather and artificial leather by Infrared spectroscopy and scanning electron microscopy, Theories and Research, No. 9, 2019.
China Search Report, Oct. 28, 2020, China.
China Patent Office, "Office Action", Mar. 11, 2021, China.

* cited by examiner

METHOD FOR AUTHENTICATION OF ANIMAL SPECIES ORIGIN OF LEATHER PRODUCTS

CROSS-REFERENCE TO RELATED APPLICATION

This application is a continuation application of International Patent Application No. PCT/CN2021/070261, filed on Jan. 5, 2021, which itself claims priority to and benefit of Chinese Patent Application No. 202010009806.2 filed on Jan. 6, 2020 in the State Intellectual Property Office of P. R. China. The disclosure of each of the above applications is incorporated herein by reference in its entirety.

FIELD OF THE INVENTION

The present invention relates to an authentication method, in particular relates to a method for authentication of animal species origin of leather products.

BACKGROUND OF THE INVENTION

Natural leather is produced from animal skins and hides, also called animal leather. Leather is widely used in clothing, shoes, suitcases, bags, belts, and other products. In recent years, with the development of market economy and the progress of science and technology, artificial leather or synthetic leather has been put into the market. During the development of leather processing, the leather-making raw materials are animal skins in the early state of leather production, among which cattle and sheep hides account for the largest proportion. The raw animal hides are subjected to tanning after a series of procedures, such as soaking, dehairing, liming, softening, and pickling. During the tanning process, tanning agent molecules penetrate the animal skins and cross-link with the active groups of collagen molecules, increasing the stability of collagen structure, improving the stability against heat and moisture, and enhancing the acid- and alkali-resistance performance. At the beginning of the 20th century, artificial leather has been mass produced. The earliest prototype of artificial leather was nitrocellulose-varnished clothing manufactured by coating nitrocellulose sol on the surface of fabrics. In the 1930s, the industrial production of polyvinyl chloride (PVC) materials gave birth to PVC artificial leather coated with PVC polymer materials, realizing their industrialization in the replacement of natural leather. In the 1960s, with the applications of polyurethane and non-woven technology in artificial leather products, polyurethane artificial leather was put into the market.

There are nearly 20 categories of natural leathers that have been used for mass production, among which genuine leather is expensive, and the price for genuine leather made of different animal skins varies substantially. There are many illegal violations that the businesses sell low-cost artificial leather while claiming as genuine leather, which infringe the rights and interests of consumers. In the field of general trade and personal consumption, there are many disputes caused by the improper labeling of leather products. Therefore, it is extremely important to authenticate whether a leather product is genuine leather and identify its animal species origin. How to authenticate natural leather rapidly and accurately, especially its animal species origin, is the focus of business and trade organizations, regulatory authorities, and consumers. It is of great significance for maintaining the healthy development of the leather industry and protecting the legitimate rights and interests of consumers.

Current authentication methods for leather products are mainly sensory inspection approaches, based on visual observation and touch feel. These approaches rely heavily on operation experience and will inevitably be influenced by the subjective judgment of operators. In addition, deoxyribonucleic acid (DNA)-based approaches have been employed for the authentication of leather species. Unfortunately, these methods are cost-, time- and labor-intensive.

SUMMARY OF THE INVENTION

The present invention aims to solve the aforementioned technical problems and provide a method for authentication of animal species origin of leather products based on rapid evaporative ionization mass spectrometry (REIMS) technology.

A method for authentication of animal species origin of leather products, which includes the following steps:

Step 1. Model Establishment:
(1) Collect leather samples from different animal species origins, set mass spectrometric parameters, cut the grain surface of leather samples using a preheated electric soldering iron, instantly producing a stream of aerosols containing a large amount of complex ion mixtures, and detect the resulting sample ions using the mass spectrometer;
(2) Import the REIMS data into the LiveID software, create a multivariate statistical model based on principal component analysis followed by linear discriminant analysis (PCA-LDA) of the REIMS data, and evaluate the model with cross-validation tests.

Step 2. Analysis of Real Leather Samples:
Open the LiveID software, select the established model, load the same mass spectrometric parameters as in Step 1, cut the surface of real leather samples using the preheated electric soldering iron, producing real-time detection results for sample analysis.

According to the method for authentication of animal species origin of leather products, the model of the electric soldering iron was CS-20 with a voltage of 220 V, a temperature of 380° C., and a full length of 170 mm;

A stream of aerosols containing a large amount of complex ion mixtures were produced during the process of cutting leather samples. An orthogonal nitrogen-driven Venturi pump at 2 bar transported the resulting aerosols through a polytetrafluoroethylene (PTFE) tube to the REIMS atmospheric interface chamber, where the aerosols collided with a heated helical coil set at the parameters of 4.5 A, 4.2 V, and 800° C.;

Afterwards, the ions from the leather samples were subjected to mass spectrometric analysis. For impurity elution, signal enhancement, and lock-mass correction, an auxiliary solution of leucine enkephalin in isopropanol at a concentration of 0.2 ng/µL was continuously infused into the REIMS source using a syringe pump. Mass drift was corrected based on the reference peaks at mass-to-charge ratio (m/z) 554.2615 in the negative ion mode and m/z 556.2771 in the negative ion mode corresponding to the deprotonated or protonated leucine enkephalin.

According to the method for authentication of animal species origin of leather products, the mass spectrometer was a quadrupole time-of-flight (QTOF) high-resolution mass spectrometer equipped with a REIMS ambient ionization source. The scan time was 1 s. The mass spectra were acquired over m/z 50-1200. Data acquisition could be carried out in either positive or negative ion mode. The negative ion mode is taken as an example to describe the method. The optimal instrument parameters optimized with the total ion current intensity and signal-to-noise ratio (S/N) values are as follows: cone voltage of 40 V, heater bias voltage of 60 V, cutting length of 1 cm, and auxiliary solvent flow rate of 0.15 mL/min. As shown in FIG. 1A, during the optimization, it was found that the total ion current intensity increased proportionately with increasing voltage from 10 to 40 V, reaching a maximum at 40 V, after which the intensity decreased dramatically and the noise increased. Similar to cone voltage, when the heater bias voltage was less than 60 V, the total ion current intensity increased incrementally with the increasing heater bias voltage. When it was greater than 60 V, the total ion current intensity tended to decline significantly. When the auxiliary solvent flow rate was less than 150 μL/min, the total ion current intensity increased with the increasing flow rate. When it was greater than 150 μL/min, the total ion current intensity steadily declined as the flow rate further increased. When the cutting length was less than 1 cm, the total ion current intensity increased significantly with the increase of the cutting length. The signal intensity plateaued as the cutting length was further increased, and the excessive cutting length adversely affected the stability of the cutting operation. The optimization of cone voltage, heater bias voltage, cutting length, and auxiliary solvent flow rate have obtained good reproducibility for the sampling and analysis protocol. Calculated based on the peak area of the total ion current, the intra-day and inter-day precision of the REIMS method were 4.68% and 7.18%, respectively.

According to the method for authentication of animal species origin of leather products, there was Step (A) between Step 1 and Step 2: Review the REIMS spectra of leather samples using the MassLynx software and examine the distribution of characteristic ions varied from leather to leather and the interspecies differences of ion responses among various leather samples.

According to the method for authentication of animal species origin of leather products, there was Step (B) after Step (A): Further analyze the REIMS data using the Progenesis QI software:

(a) Peak alignment: The REIMS raw data from all the leather samples were imported into the Progenesis QI software, where the ion peaks were automatically aligned for correct comparison of compounds in different leather samples.

(b) Grouping: All the data were grouped based on animal leather categories.

(c) Peak extraction: The peaks in the raw data were detected for discovering the compounds in leather samples.

(d) Deconvolution: After peak extraction, the ions in different adduct forms for the same compound in leather samples were grouped, calculating the neutral mass of the compound based on the mass difference between various adduct forms. When the variable importance in projection (VIP) score of a compound was greater than 1, the result validity for the compound was reviewed by deconvolution. Select the compound in the left list, and then check the result using the visualized graph in the rest part of the screen. First, use deconvolution matrix to find any apparent problems. If there was uncertainty for an ion, check whether its mass spectrum matched other ions of the compound.

(e) Compound identification: Identify the compounds that may possibly exist in various animal leathers with the following procedure: Select identification method of Progenesis MetaScope; Select the search parameter of Tutorial No Fragmentation; Select the compound database of Basic lipids; Set the mass accuracy of <5 ppm and the retention time deviation within 0.1 min.

(f) Compound identification results review: Check all the identified compounds in animal leathers with VIP scores above 1 in detail.

(g) Comprehensive statistical analysis: Principal component analysis (PCA) uses the compound abundance level to find the principal axis for abundance changes, transforming and plotting the abundance data in the principal component space. The partial least square-discriminant analysis (PLS-DA) model was established by separating the running samples according to the abundance changes. The data from the same animal origin were clustered into the same region, while the data from different animal origins featured complete spatial separation;

Based on grouping conditions, the interspecies differences between individual animal leather categories were analyzed. The VIP-variable importance plot for the multivariate statistical analysis displayed the relative influence of each ion on all responses in decreasing VIP score order from the most influential to the least influential. As to the VIP versus PLS coefficients, important x variable had higher positive VIP scores and greater positive or negative coefficient values, revealing the prominent marker compounds that highly contributed to the discriminant separation model between leather species;

(h) Find out the potential marker compounds for each leather sample and determine the relative content of the main compounds.

According to the method for authentication of animal species origin of leather products, there was Step 3 after Step 2: High-resolution scanning electron microscopy (SEM) was used to characterize the muscle face fibers and cross sections of leather samples; Or if the real-time recognition result using the REIMS method was negative, it indicated that the sample did not belong to any animal leather category investigated in the model. For instance, for a split cattle leather sample, the grain surface layer consisted of synthetic materials and the muscle surface layer consisted of dermal fibers. SEM could be used to observe the microstructures of muscle surface layer of the leather sample to determine whether the muscle surface layer consisted of natural leather fibers;

The characterization method included the following steps: A small number of fibers from the muscle surface layer of the leather sample was adhered to the conductive adhesive of a sample plate using a tweezer, then gold sputtered for 160 s. The microstructures of the leather fibers were characterized using SEM operated at a working voltage of 15.0 kV, a magnification of 60000-80000 times, and a working distance of 12200 μm.

The differences between the invention and current techniques are as follows:

The invention established a method for authentication of animal species origin of leather products that can overcome the subjective influence of operators. Without the need of any sample pretreatment, the invention can accurately discriminate between synthetic leather and natural leather and identify the interspecies differences of genuine leathers from different animal origins, thus revealing the identity of the detected leather products objectively and rapidly.

The SEM method involved in the present invention can clearly characterize the fiber microstructures of muscle surface layer of natural leather, which are obviously different to artificial fiber, thereby facilitating the objective discrimination between natural leather fiber and artificial fiber.

The invention for authentication of animal species origin of leather products is further explained in combination with the following attached figures.

BRIEF DESCRIPTION OF THE DRAWINGS

Additional objectives, functions, and advantages of the present invention will be set forth in the description of embodiments which follow, with reference to the accompanying drawings in which.

DETAILED DESCRIPTION OF THE INVENTION

1. Instrument and software
1.1 The model of the electric soldering iron: CS-20; Manufacturer: TAIYO ELECTRIC IND. CO., LTD
1.2 Ion source and mass spectrometer information A QTOF high-resolution mass spectrometer equipped with a REIMS ambient ionization source; Model: Xevo G2-XS; Manufacturer: Waters Corporation.
1.3 Software information
MassLynx 4.1, Live ID, Progenesis QI 2.4, EZ info 3.0: Waters Corporation.
1.4 Scanning electron microscope
Model: Hitachi S-4800.

Embodiment 1

A method for authentication of animal species origin of leather products, which includes the following steps:
Step 1. Model Establishment:
 (1) Collect leather samples from different animal species origins, set mass spectrometric parameters, cut the grain surface of leather samples using a preheated electric soldering iron, instantly producing a stream of aerosols containing a large amount of complex ion mixtures, and detect the resulting sample ions using the mass spectrometer;

The model of the electric soldering iron was CS-20 with a voltage of 220 V, a temperature of 380° C., and a full length of 170 mm;

A stream of aerosols containing a large amount of complex ion mixtures were produced during the process of cutting leather samples. An orthogonal nitrogen-driven Venturi pump at 2 bar transported the resulting aerosols through a PTFE tube to the REIMS atmospheric interface chamber, where the aerosols collided with a heated helical coil set at the parameters of 4.5 A, 4.2 V, and 800° C.;

Afterwards, the ions from leather samples were subjected to mass spectrometric analysis. For impurity elution, signal enhancement, and lock-mass correction, an auxiliary solution of leucine enkephalin in isopropanol at a concentration of 0.2 ng/µL was continuously infused into the REIMS source using a syringe pump. Mass drift was corrected based on the reference peaks at m/z 554.2615 in the negative ion mode and m/z 556.2771 in the negative ion mode corresponding to the deprotonated or protonated leucine enkephalin.

Figure 1A:
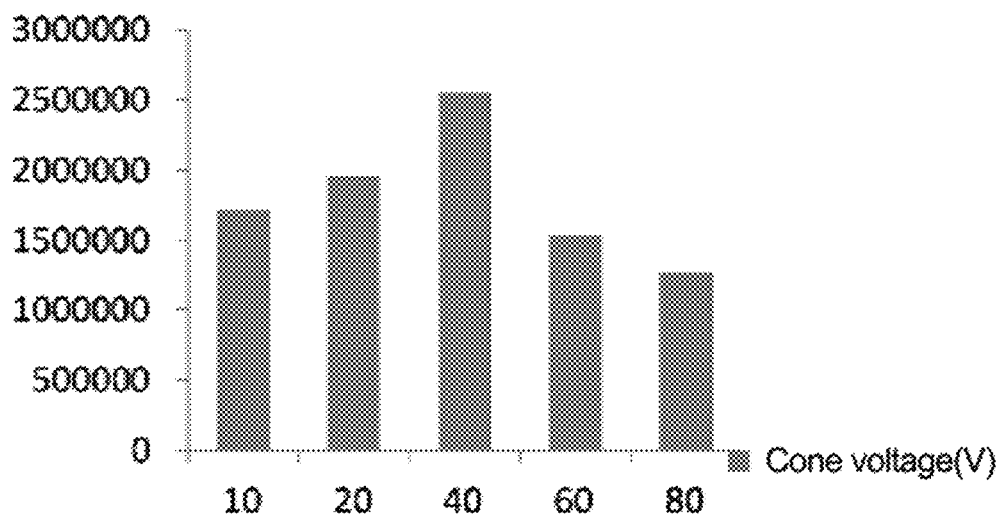
FIG. 1A is the diagram for the optimization of cone voltage.
Figure 1B:
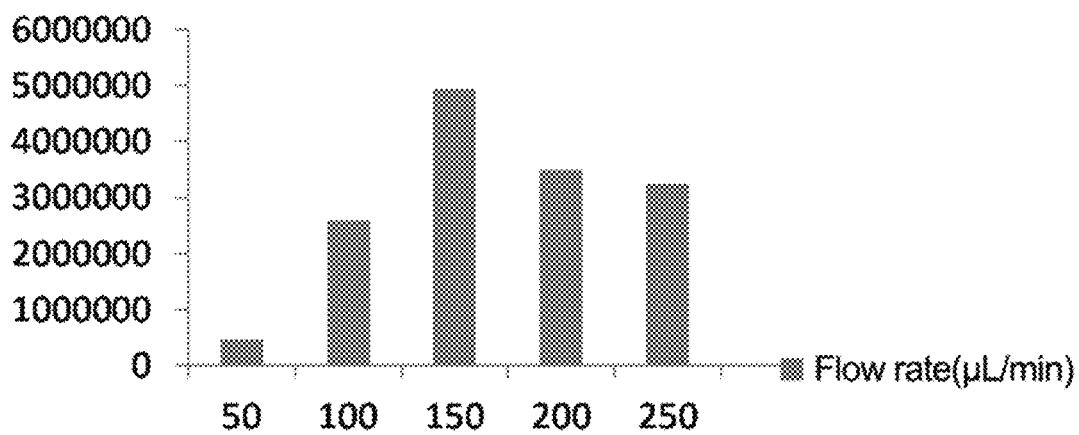
FIG. 1B is the diagram for the optimization of auxiliary solvent flow rate.
Figure 1C:
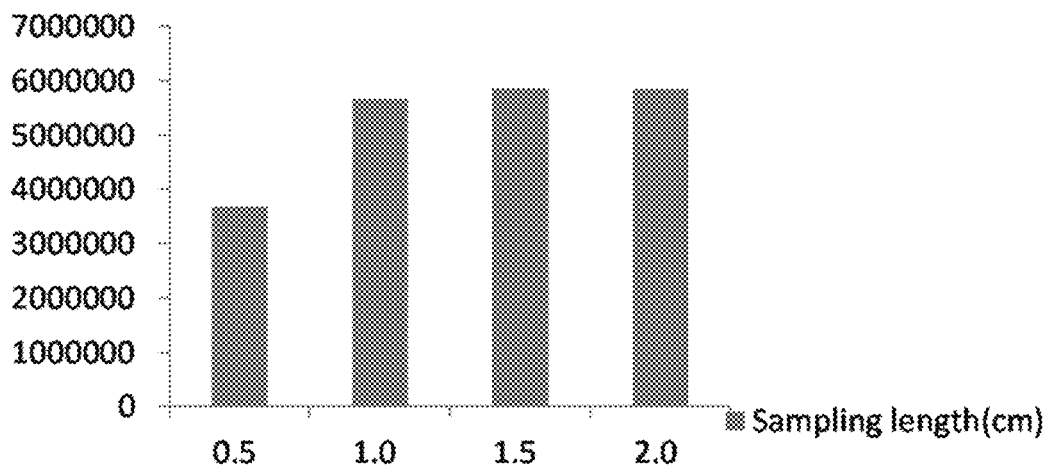
FIG. 1C is the diagram for the optimization of sampling length.
Figure 1D:
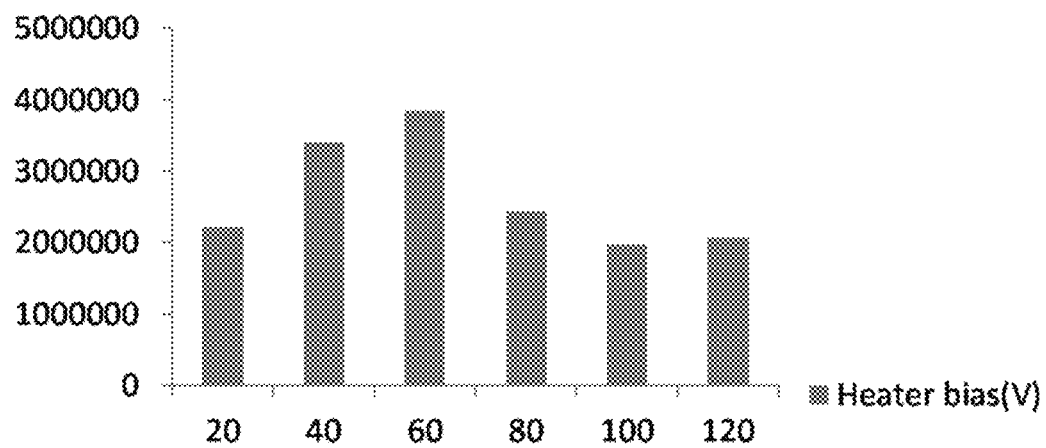
FIG. 1D is the diagram for the optimization of heater bias voltage.

The mass spectrometer was a QTOF high-resolution mass spectrometer equipped with a REIMS ambient ionization source. The scan time was 1 s. The mass spectra were acquired over m/z 50-1200. Data acquisition could be carried out in either positive or negative ion mode;

The instrument parameters were optimized based on the total ion current intensity and S/N values. As shown in FIG. 1A, the optimal cone voltage was 40 V. As shown in FIG. 1B, the optimal auxiliary solvent flow rate was 0.15 mL/min (150 µL/min). As shown in FIG. 1C, the optimal sampling length was 1.0 cm. As shown in FIG. 1D, the optimal heater bias voltage was 60 V.

(2) Import the REIMS data into the LiveID software, create a multivariate statistical model based on PCA-LDA analysis of the REIMS data, and evaluate the model with cross-validation tests.

Step 2. Analysis of Real Leather Samples:
Open the LiveID software, select the established model, load the same mass spectrometric parameters as in Step 1, cut the surface of real leather samples using the preheated electric soldering iron, producing real-time detection results for sample analysis.

Embodiment 2

A method for authentication of animal species origin of leather products, which includes the following steps:

I. Analysis of Genuine Leather Samples from Different Animal Origins Based on REIMS Technology:

A preheated electric soldering iron (a kind of handheld sampling device with electrothermal probe) (CS-20, voltage of 220 V, temperature of 380° C., and full length of 170 mm) was used to cut the surface of leather samples;

A stream of aerosols containing a large amount of complex ion mixtures were produced during the process of cutting leather samples. An orthogonal nitrogen-driven Venturi pump at 2 bar transported the resulting aerosols through a PTFE tube to the REIMS atmospheric interface chamber, where the aerosols collided with a heated helical coil (4.5 A, 4.2 V, and 800° C.). Afterwards, the ions from leather samples were subjected to mass spectrometric analysis. For impurity elution, signal enhancement, and lock-mass correction, an auxiliary solution of leucine enkephalin in isopropanol at a concentration of 0.2 ng/μL was continuously infused into the REIMS source using a syringe pump. Mass drift was corrected based on the reference peaks at m/z 554.2615 in the negative ion mode and m/z 556.2771 in the negative ion mode corresponding to the deprotonated or protonated leucine enkephalin. The mass spectrometer was a QTOF high-resolution mass spectrometer equipped with a REIMS ambient ionization source. The scan time was 1 s. The mass spectra were acquired over m/z 50-1200. Data acquisition could be carried out in either positive or negative ion mode.

The mass spectrometric parameters are as follows: cone voltage of 40 V, heater bias voltage of 60 V, cutting length of 1 cm, and auxiliary solvent flow rate of 0.15 mL/min.

II. Model Establishment and Cross-Validation

Figure 2:
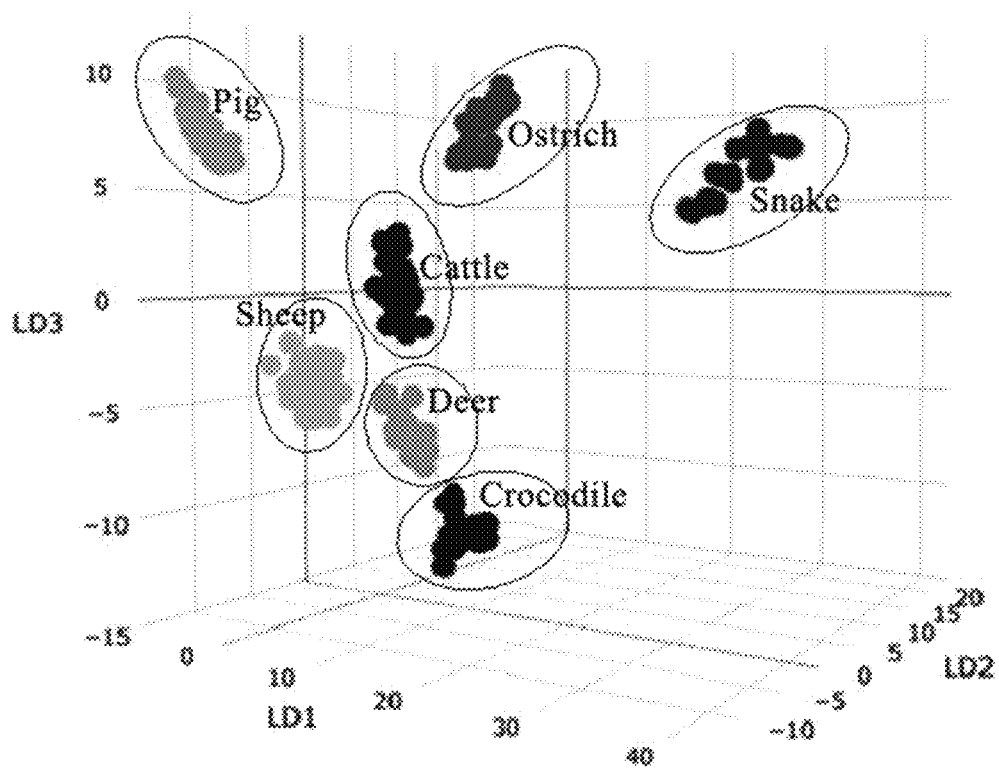
FIG. 2 is the PCA-LDA chemometric model based on REIMS analysis of seven categories of animal leathers.

Import the REIMS data obtained from different animal leathers into the LiveID software, which were grouped and named according to different animal origins. With the aid of the LiveID software, create a multivariate statistical model based on PCA-LDA analysis of the REIMS data, and evaluate the model with cross-validation tests. The PCA-LDA scatter plot for the seven categories of animal leathers is shown in FIG. 2 (cattle leather is represented by a solid circle, sheep leather by a hollow square, pig leather by a hollow circle, deer leather by a diamond, ostrich leather by a star, crocodile leather by a triangle, snake leather by a solid square; each type of leather was sampled 10 to 60 times). After the model was established, it was subjected to cross-validation. The validation method was implemented to verify the model accuracy by excluding a group of samples. Table 1 is an example of the cross-validation results of the PCA-LDA model for the seven categories of animal leathers. The cross-validation accuracy of the model was 98.22%.

TABLE 1

Cross-validation results of the PCA-LDA model for the seven categories of leathers.

| | | | | | | | |
|---|---|---|---|---|---|---|---|
| Outlier threshold | | | | | | | 10 |
| Principal components in principal component analysis | | | | | | | 20 |
| Linear discriminant | | | | | | | 6 |

Validation parameters

| Validation type | 5 times |
|---|---|

Result summary

| | Mass spectra | Pass | Failure | Outlier | Accuracy |
|---|---|---|---|---|---|
| Total | 281 | 276 | 1 | 4 | 98.22% |

Hybrid matrix

| | Cattle | Sheep | Pig | Deer | Ostrich | Crocodile | Snake | Outlier | Total |
|---|---|---|---|---|---|---|---|---|---|
| Cattle | 58 | 0 | 0 | 0 | 0 | 0 | 0 | 1 | 59 |
| Sheep | 0 | 73 | 0 | 0 | 0 | 0 | 0 | 0 | 73 |
| Pig | 0 | 0 | 50 | 0 | 0 | 0 | 0 | 0 | 50 |
| Deer | 0 | 0 | 0 | 31 | 0 | 1 | 0 | 1 | 33 |
| Ostrich | 0 | 0 | 0 | 0 | 29 | 0 | 0 | 0 | 29 |
| Crocodile | 0 | 0 | 0 | 0 | 0 | 17 | 0 | 1 | 18 |
| Snake | 0 | 0 | 0 | 0 | 0 | 0 | 18 | 1 | 19 |

Figure 3:
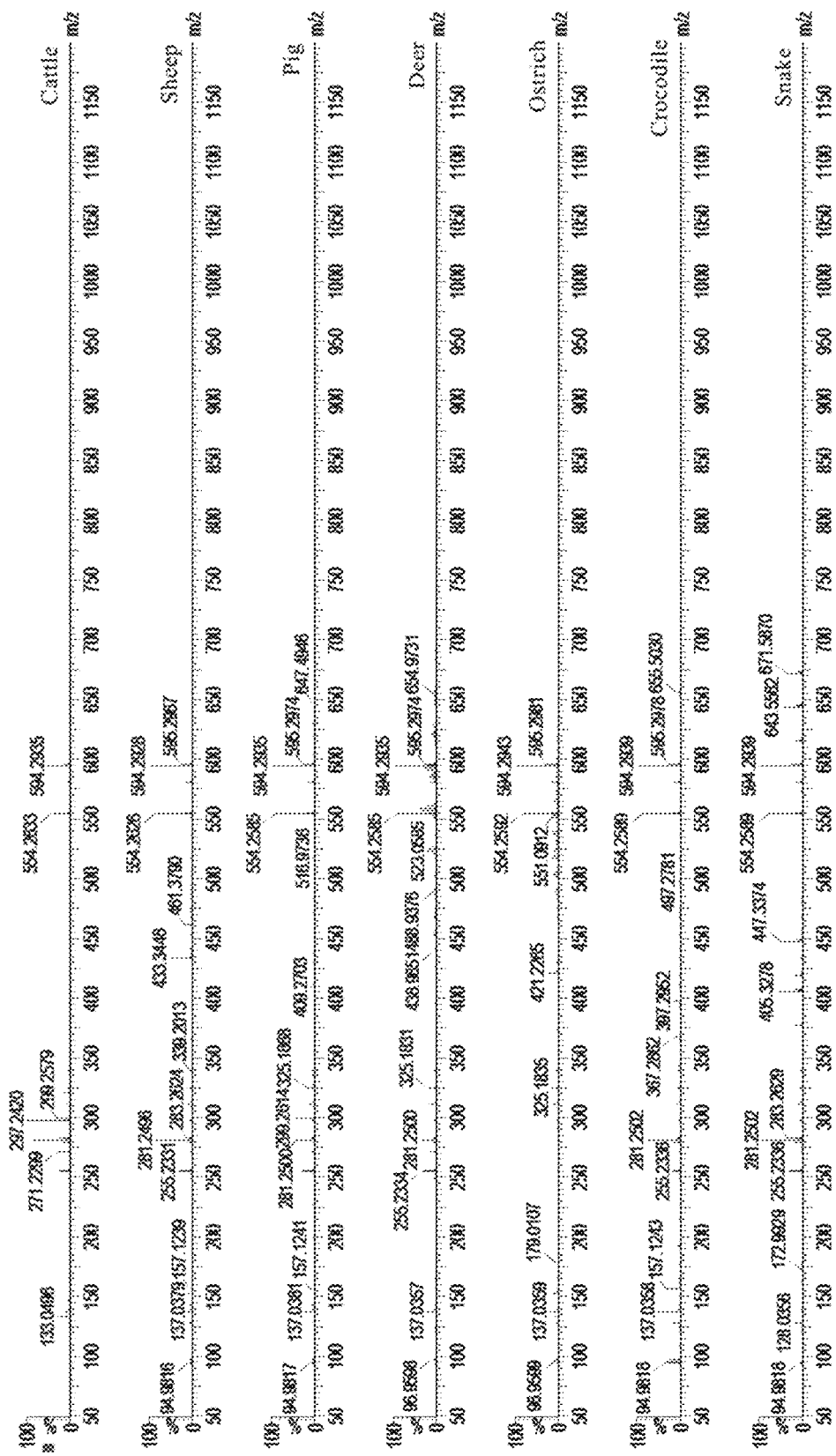
FIG. 3 are the mass spectra for the analysis of seven categories of animal leathers.

III. Examination of the REIMS Spectra of Leather Samples via the MassLynx Software FIG. 3 exhibits the exemplary mass spectra of seven categories of natural animal leathers. The figure shows that the mass spectrometric information of animal leathers is mainly concentrated in a small molecular mass region (m/z 200-400). The mass spectrometric information of deer and ostrich leathers is comprehensive at m/z 500-650. The distribution of characteristic ions varies from leather to leather and the interspecies differences of ion responses among various leather samples can be examined.

IV. Further Analysis of the REIMS Data Using the Progenesis QI Software (a) Peak alignment: The REIMS raw data from all the leather samples were imported into the Progenesis QI software, where the ion peaks were automatically aligned for correct comparison of compounds in different leather samples. This a critical stage for the entire workflow. The key point is inputting all the data into the correct queue, thus facilitating correct peak picking and rapid and robust statistical analysis.

(b) Grouping: All the data were grouped based on animal leather categories.

(c) Peak extraction: The peaks in the raw data were detected for discovering the compounds in leather samples.

(d) Deconvolution: After peak extraction, the ions in different adduct forms for the same compound in leather samples were grouped, calculating the neutral mass of the compound based on the mass difference between various adduct forms. When the VIP score of a compound was greater than 1, the result validity for the compound was reviewed by deconvolution. Select the compound in the left list, and then check the result using the visualized graph in the rest part of the screen. First, use deconvolution matrix to find any apparent problems. If there was uncertainty for an ion, check whether its mass spectrum matched other ions of the compound.

(e) Compound identification: Identify the compounds that may possibly exist in various animal leathers with the following procedure: Select identification method of Progenesis MetaScope; Select the search parameter of Tutorial No Fragmentation; Select the compound database of Basic lipids; Set the mass accuracy of <5 ppm and the retention time deviation within 0.1 min.

(f) Compound identification results review: Check all the identified compounds in animal leathers with VIP scores above 1 in detail. The compounds of interest refer to the compound with the VIP scores above 1 in the VIP-variable importance plot. Moreover, the compounds with statistical significance (p-value<0.05 in t-test) and max fold change above 2 can be filtered.

Figure 4A:
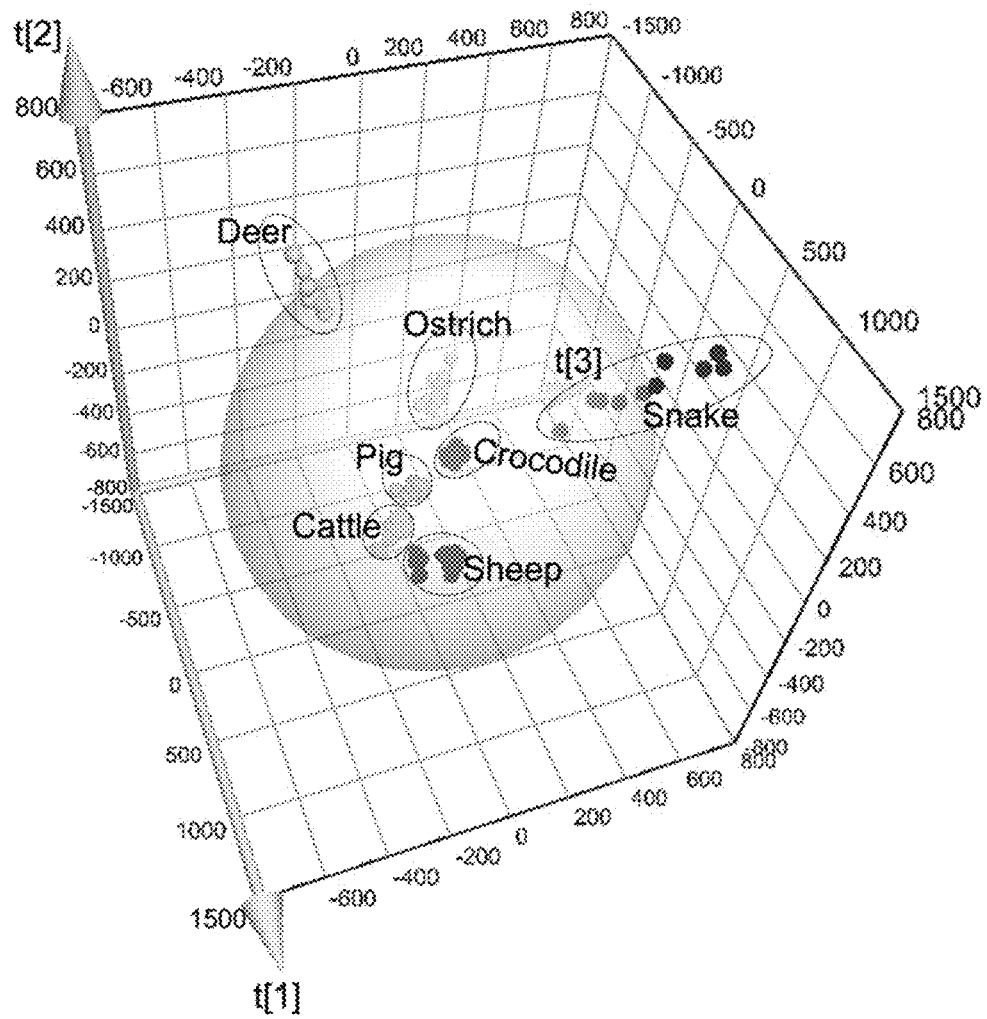
FIG. 4A is the PLS-DA three-dimensional score plot of principal components 1, 2, and 3 based on REIMS analysis of seven categories of animal leathers.
Figure 4:
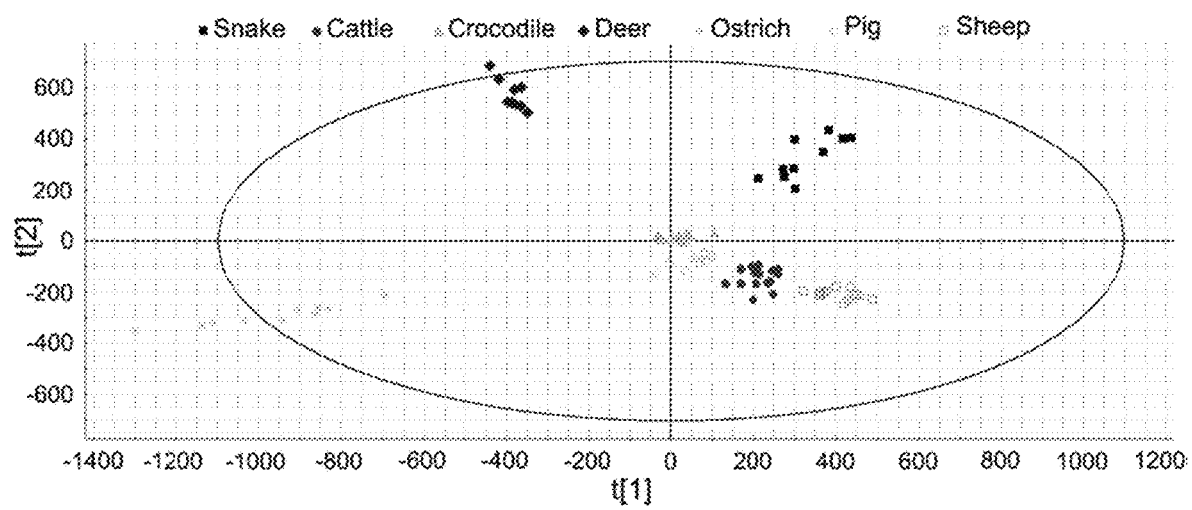
FIG. 4B is the PLS-DA score plot of principal components 1 and 2 based on REIMS analysis of seven categories of animal leathers.
Figure 5:
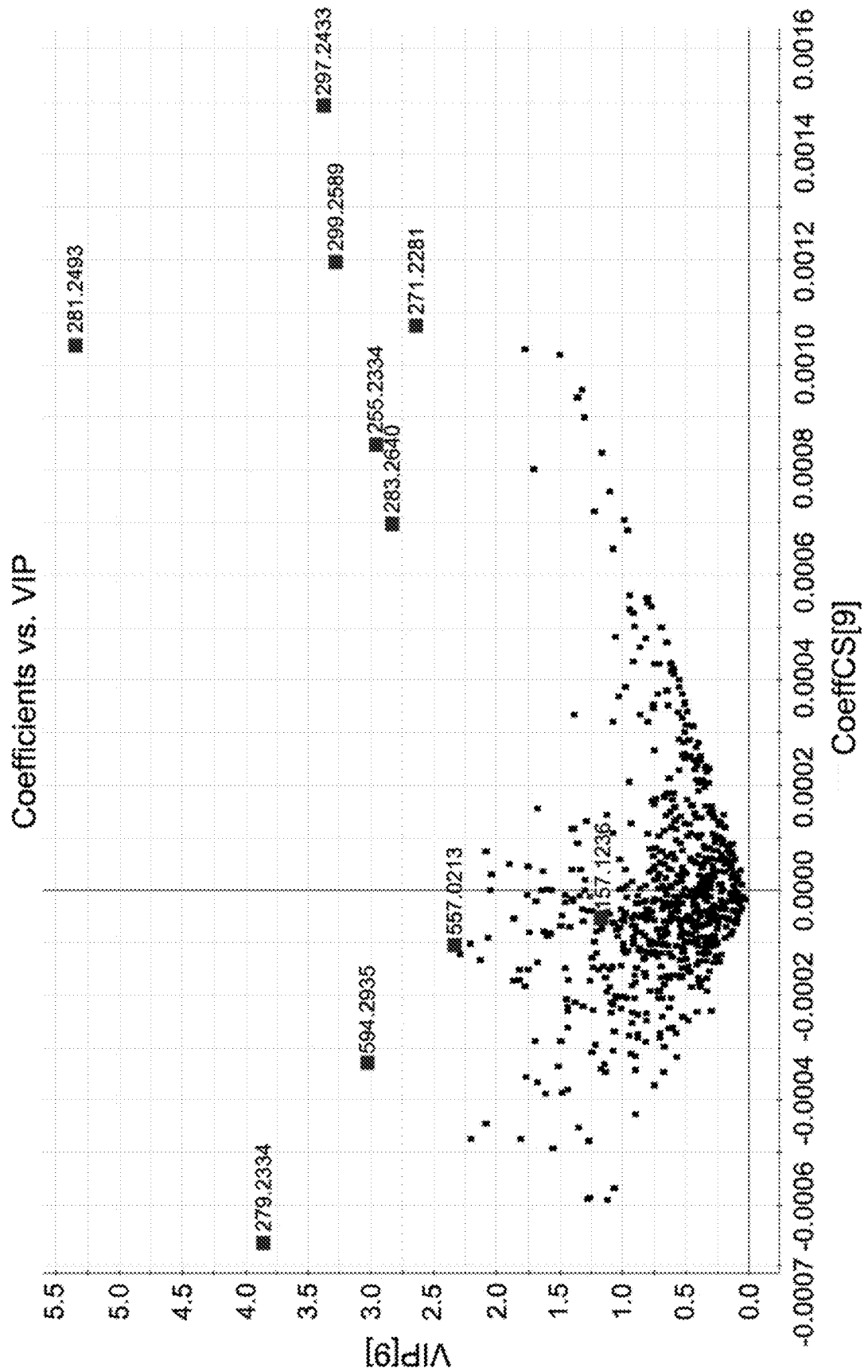
FIG. 5 is the VIP-variable importance plot of the PLS-DA model for seven categories of animal leathers.

(g) Comprehensive statistical analysis: PCA uses the compound abundance level to find the principal axis for abundance changes, transforming and plotting the abundance data in the principal component space. The PLS-DA model was established by separating the running samples according to the abundance changes. The data from the same animal origin were clustered into the same region, while the data from different animal origins featured complete spatial separation. FIG. 4A shows the PLS-DA three-dimensional score plot of principal components 1, 2, and 3 based on REIMS analysis of seven categories of animal leathers. FIG. 4B shows the PLS-DA score plot of principal components 1 and 2 based on REIMS analysis of seven categories of animal leathers. Based on grouping conditions, the interspecies differences between individual animal leather categories were analyzed. The VIP-variable importance plot for the multivariate statistical analysis displayed the relative influence of each ion on all responses in decreasing VIP score order from the most influential to the least influential. FIG. 5 shows the VIP versus PLS coefficients. Important x variable had higher positive VIP scores and greater positive or negative coefficient values, revealing the prominent marker compounds that highly contributed to the discriminant separation model between leather species. For example, the ion at m/z 281.2493 had a VIP score of 5.3425 and a great positive coefficient value, illustrating that the ion at m/z 281.2493 had a major influence on the classification of the leathers from different animal origins. It was tentatively identified as a $C_{18}$-unsaturated fatty acid with a double bond by searching against the LIPID MAPS Structure Database.

(h) Find out the potential marker compounds for each leather sample and determine the relative content of the main compounds (Table 2 and Table 3).

TABLE 2

Possible fatty acid chain compositions in different animal leathers identified based on the REIMS method.

| No. | VIP | Theoretical (m/z) | Measured (m/z) | Adduct ion | Neutral mass (Da) | Formula | Score | Mass error (ppm) | Isotope similarity | Identity | Origin |
|---|---|---|---|---|---|---|---|---|---|---|---|
| 1 | 5.34 | 281.2492 | 281.2491 | $[M - H]^-$ | 282.2566 | $C_{18}H_{34}O_2$ | 35.9 | 1.9189 | 81.6847 | C18:1 | Sheep |
| 2 | 3.87 | 279.2332 | 279.2334 | $[M - H]^-$ | 280.2406 | $C_{18}H_{32}O_2$ | 36.0 | 1.4776 | 81.70347 | C18:2 | Sheep |
| 3 | 3.38 | 297.2435 | 297.2433 | $[M - H]^-$ | 298.2506 | $C_{18}H_{34}O_3$ | 36.1 | -0.7792 | 81.48965 | C18:1; O | Pig |
| 4 | 3.28 | 299.2589 | 299.2589 | $[M - H]^-$ | 300.2661 | $C_{18}H_{36}O_3$ | 38.1 | -1.0517 | 91.55914 | C18:0; O | Pig |
| 5 | 2.91 | 255.2333 | 255.2334 | $[M - H]^-$ | 256.2407 | $C_{16}H_{32}O_2$ | 38.0 | 1.8542 | 92.01411 | C16:0 | Cattle |
| 6 | 2.63 | 271.2279 | 271.2283 | $[M - H]^-$ | 272.2354 | $C_{16}H_{32}O_3$ | 36.3 | 1.4804 | 83.27811 | C16:0; O | Cattle |
| 7 | 1.18 | 157.1234 | 157.1236 | $[M - H]^-$ | 158.1308 | $C_9H_{18}O_2$ | 37.7 | 1.4123 | 90.18968 | C9:0 | Crocodile |
| 8 | 5.72 | 283.2643 | 283.2639 | $[M - H]^-$ | 284.2713 | $C_{18}H_{36}O_2$ | 36.1 | -1.0815 | 81.66595 | C18:0 | Snake |

TABLE 3

Relative contents of the major small-molecule lipid compounds in leathers from different animal origins.

| | Measured ion (m/z) | Cattle | | Sheep | | Pig | | Deer | | Ostrich | | Crocodile | | Snake | |
|---|---|---|---|---|---|---|---|---|---|---|---|---|---|---|---|
| No. | | Intensity (cps, $10^4$) | Content (%) | Intensity (cps, $10^4$) | Content (%) | Intensity (cps, $10^4$) | Content (%) | Intensity (cps, $10^4$) | Content (%) | Intensity (cps, $10^4$) | Content (%) | Intensity (cps, $10^4$) | Content (%) | Intensity (cps, $10^4$) | Content (%) |
| 1 | 281.2491 | 266.00 | 25.60 | 128.00 | 53.63 | 40.40 | 27.58 | 71.6 | 39.70 | 9.7 | 26.81 | 116 | 46.32 | 273 | 43.76 |
| 2 | 279.2334 | 41.30 | 3.97 | 19.0 | 7.96 | 2.74 | 1.87 | 17.0 | 9.43 | 2.80 | 7.74 | 25.0 | 9.98 | 54.90 | 8.80 |
| 3 | 297.2433 | 349.00 | 33.58 | 13.20 | 5.53 | 6.08 | 4.15 | 3.53 | 1.96 | 0.59 | 1.63 | 12.20 | 4.87 | 17.6 | 2.82 |
| 4 | 299.2589 | 132.00 | 12.70 | 3.25 | 1.36 | 46.40 | 31.68 | 2.89 | 1.60 | 0.56 | 1.55 | 3.74 | 1.49 | 17.0 | 2.72 |
| 5 | 255.2334 | 72.20 | 6.95 | 47.80 | 20.03 | 27.50 | 18.77 | 47.9 | 26.56 | 7.46 | 20.62 | 26.0 | 10.38 | 113.00 | 18.11 |
| 6 | 271.2283 | 98.10 | 9.44 | 3.65 | 1.53 | 5.14 | 3.51 | 15.7 | 8.70 | 0.27 | 0.75 | 5.79 | 2.31 | 6.49 | 1.04 |
| 7 | 157.1236 | 3.90 | 0.38 | 9.46 | 3.96 | 9.57 | 6.53 | 6.45 | 3.58 | 10.3 | 28.47 | 47.4 | 18.93 | 8.89 | 1.42 |
| 8 | 283.2639 | 76.70 | 7.38 | 14.30 | 5.99 | 8.65 | 5.91 | 15.3 | 8.48 | 4.50 | 12.44 | 14.3 | 5.71 | 133 | 21.3 |

IV. SEM characterization of the muscle face fibers and cross sections of leather samples; Or if the real-time recognition result using the REIMS method was negative, it indicated that the sample did not belong to any animal leather category investigated in the model. For instance, for a split cattle leather sample, the grain surface layer consisted of synthetic materials and the muscle surface layer consisted of dermal fibers. SEM could be used to observe the microstructures of muscle surface layer of the leather sample to determine whether the muscle surface layer consisted of natural leather fibers;

The characterization method included the following steps: A small number of fibers from the muscle surface layer of the leather sample was adhered to the conductive adhesive of a sample plate using a tweezer, then gold sputtered for 160 s. The microstructures of the leather fibers were characterized using SEM operated at a working voltage of 15.0 kV, a magnification of 60000-80000 times, and a working distance of 12200 μm.

Figure 7A:
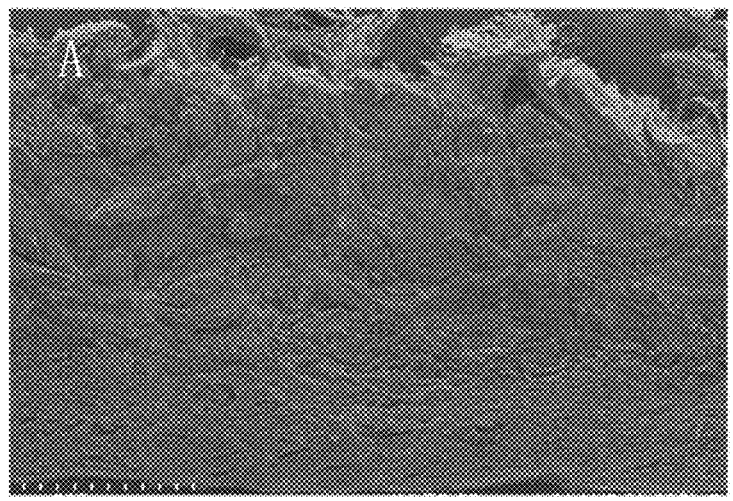
FIG. 7A is the high-resolution SEM image for the characterization of cattle leather.
Figure 7B:
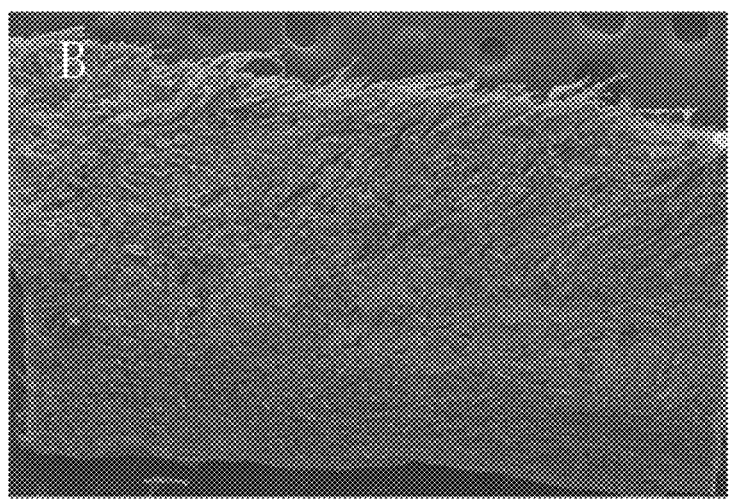
FIG. 7B is the high-resolution SEM image for the characterization of sheep leather.
Figure 7C:
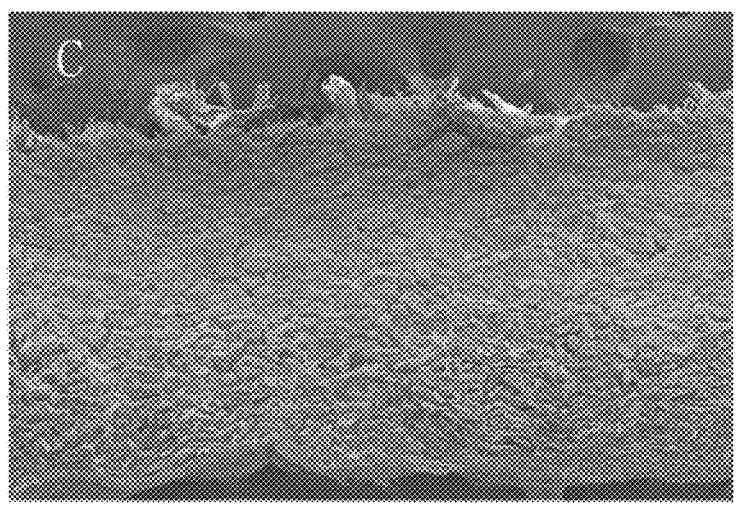
FIG. 7C is the high-resolution SEM image for the characterization of pig leather.
Figure 7D:
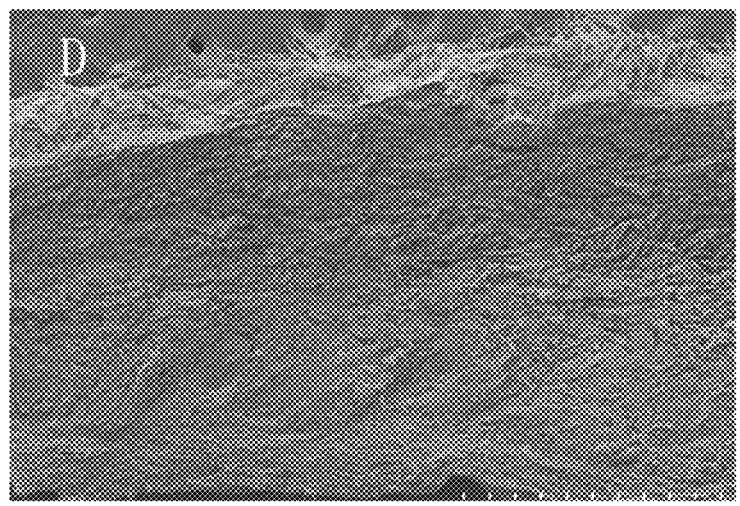
FIG. 7D is the high-resolution SEM image for the characterization of deer leather.
Figure 7E:
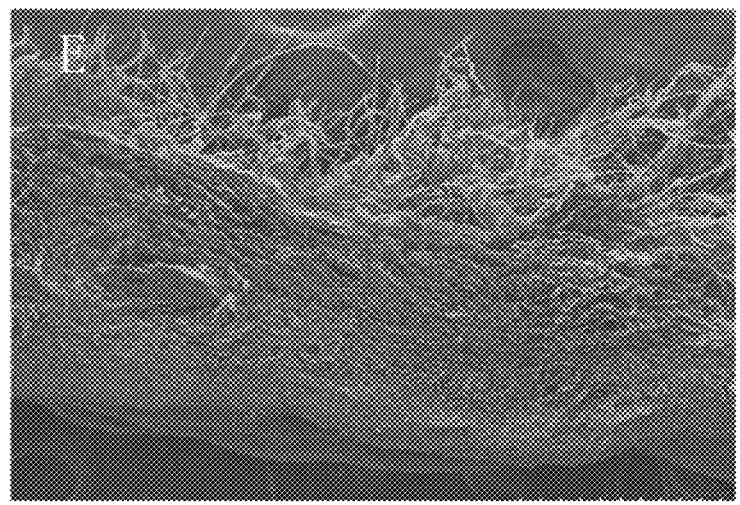
FIG. 7E is the high-resolution SEM image for the characterization of ostrich leather.
Figure 7F:
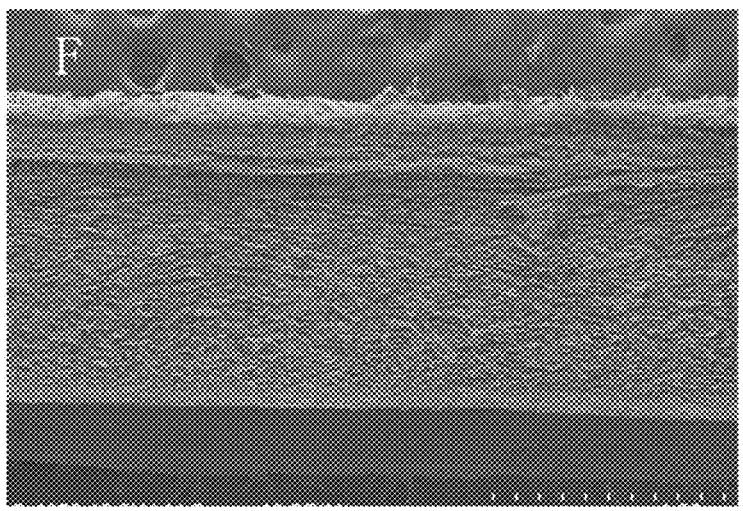
FIG. 7F is the high-resolution SEM image for the characterization of crocodile leather.
Figure 7G:
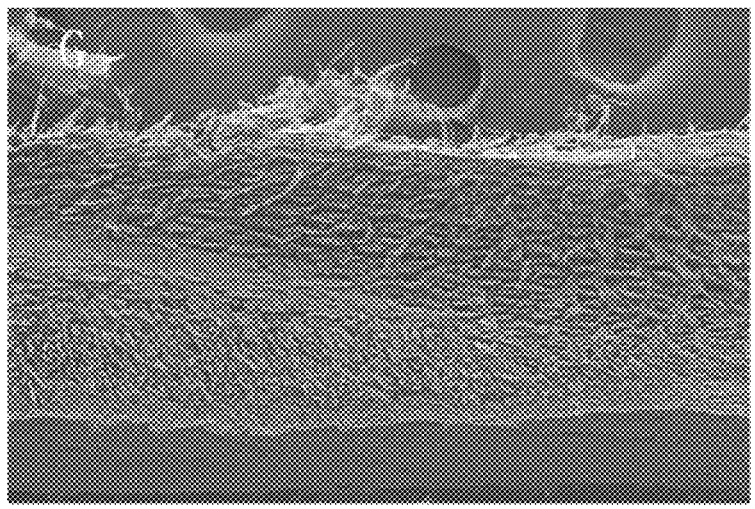
FIG. 7G is the high-resolution SEM image for the characterization of snake leather.
Figure 7H:
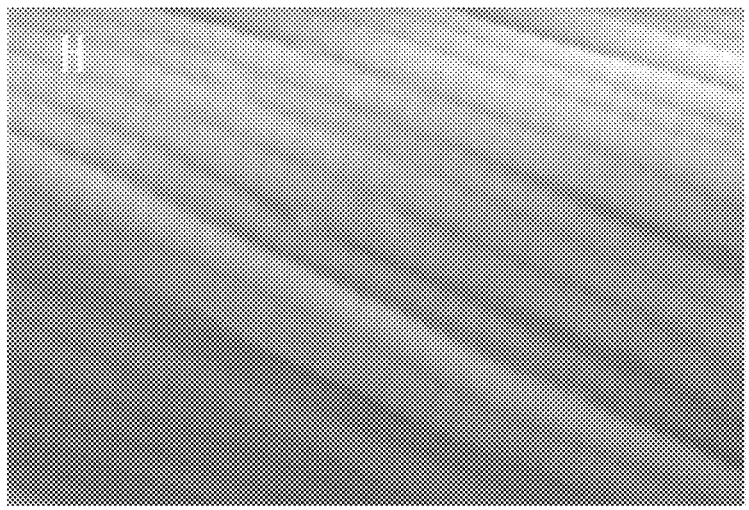
FIG. 7H is the high-resolution SEM image for the characterization of natural animal leather muscle fibers with helical microstructures (an exemplary sample of pig leather muscle fibers).
Figure 7I:
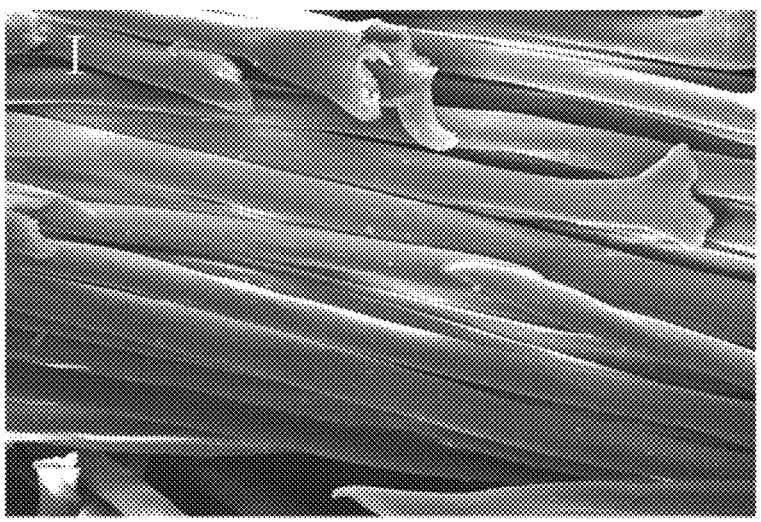
FIG. 7I is the high-resolution SEM image for the characterization of artificial fiber microstructures.

The traditional method attaches the cross section of leather samples that have been cut on the conductive adhesive. Meanwhile, when SEM is used for observation with a high magnification, the cross-section fibers in the muscle surface layer are mostly in a drifting state. The microstructures of the fibers in natural leathers cannot be clearly observed because the fibers are not being fixed on the sample plate separately. FIG. 7A is the high-resolution SEM image for the characterization of cattle leather. FIG. 7B is the high-resolution SEM image for the characterization of sheep leather. FIG. 7C is the high-resolution SEM image for the characterization of pig leather. FIG. 7D is the high-resolution SEM image for the characterization of deer leather. FIG. 7E is the high-resolution SEM image for the characterization of ostrich leather. FIG. 7F is the high-resolution SEM image for the characterization of crocodile leather. FIG. 7G is the high-resolution SEM image for the characterization of snake leather. FIG. 7I is the high-resolution SEM image for the characterization of artificial fiber microstructures. The SEM method involved in the present invention overcomes the drifting characteristics of the fiber under characterization and can clearly observe that all the natural leather muscle fibers have helical microstructures as shown in FIG. 7H, which are obviously different from the artificial fibers.

V. Real-Time Analysis of Actual Samples

Figure 6A:
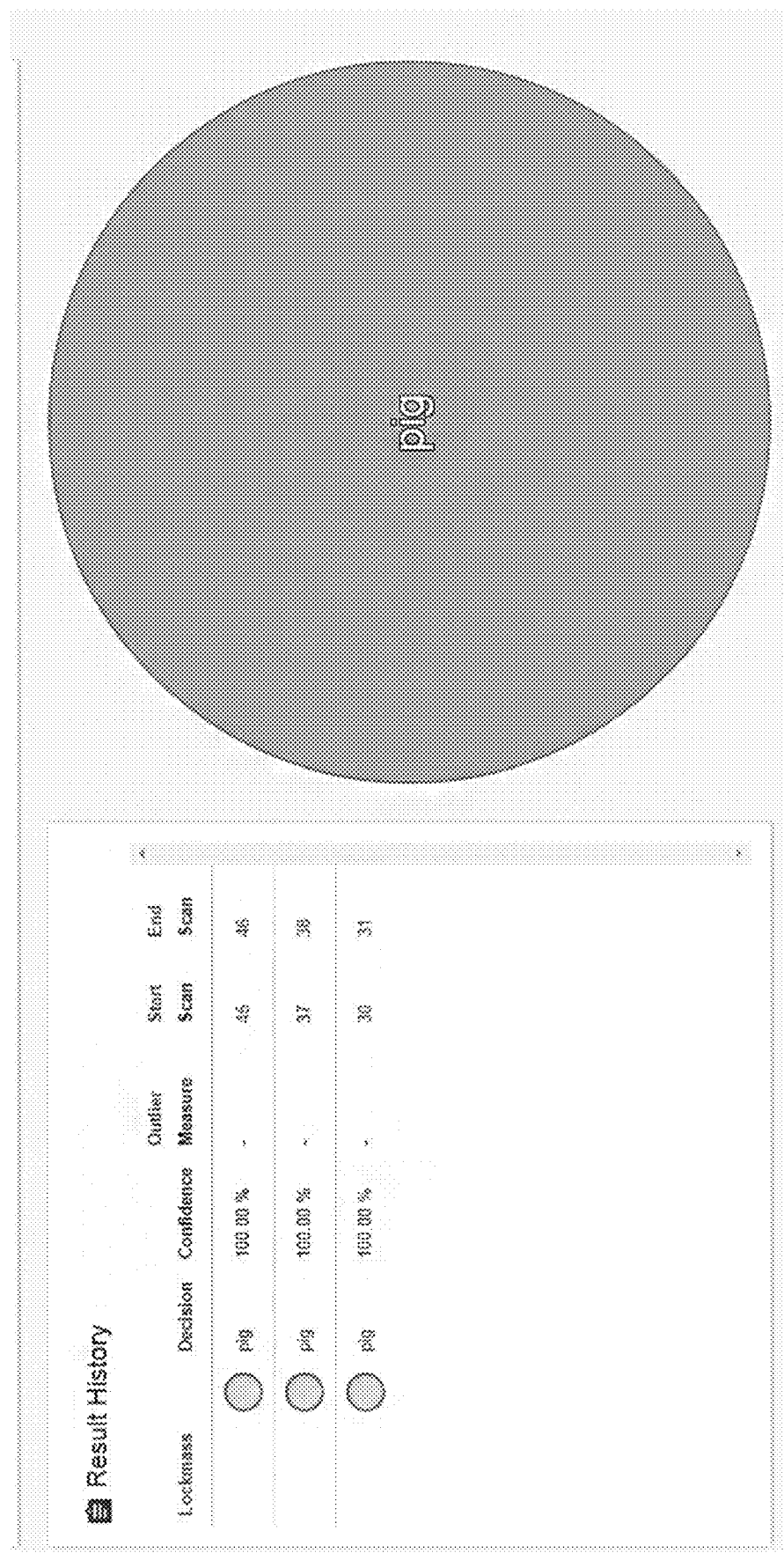
FIG. 6A is the diagram of real-time testing result for a pig leather sample.
Figure 6B:
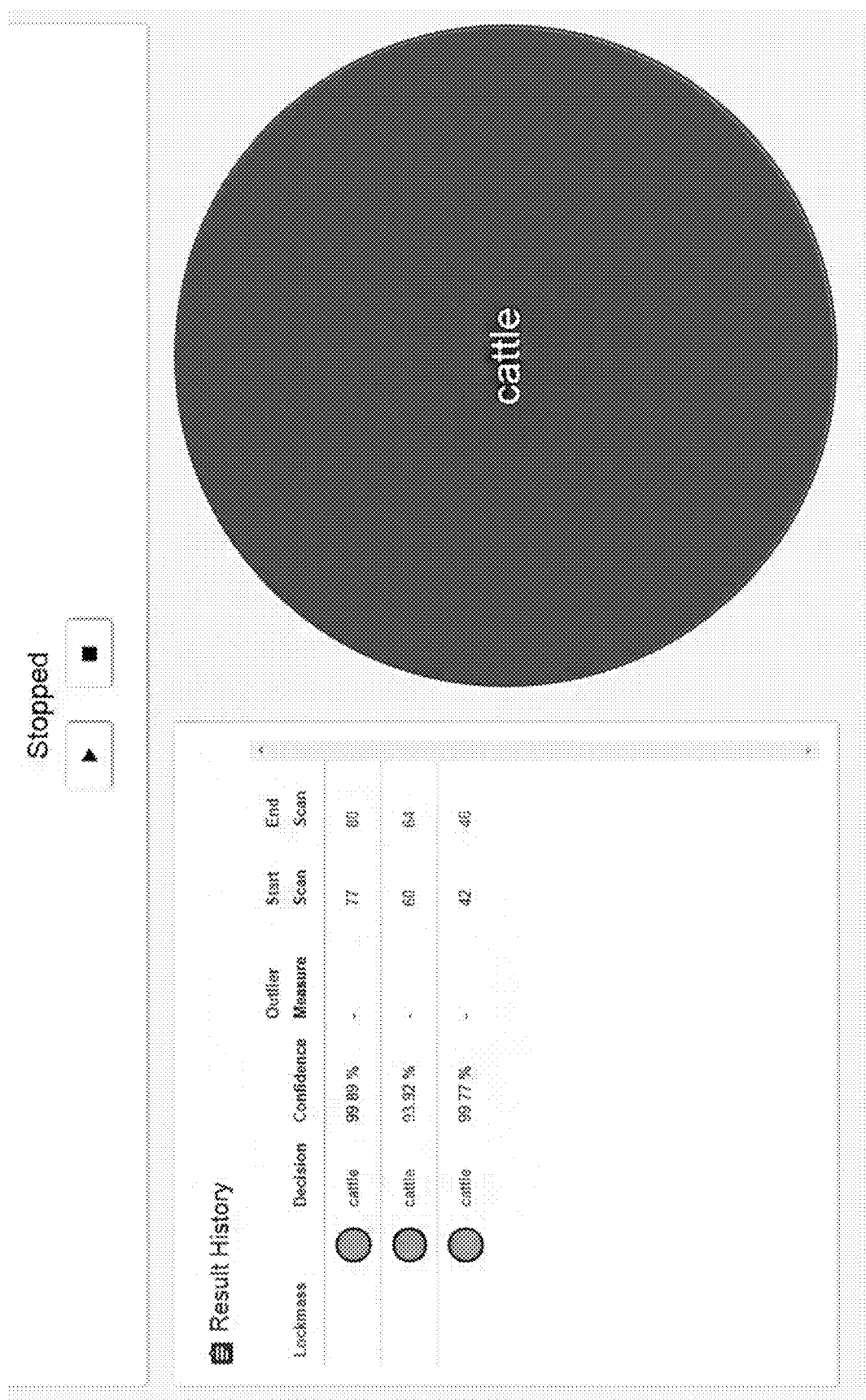
FIG. 6B is the diagram of real-time testing result for a cattle leather sample.

The LiveID software in combination with the REIMS technology enables us to establish the chemometric model to quickly authenticate the real identity of leather products, which could hardly be identified. After cross-validation of the model, open the LiveID software, select the established model, cut the leather sample, run the same instrument parameters as during model establishment, almost instantly the detection results can be obtained. The direct answer about the real identity of the sample can be provided within only several seconds. The proposed method was applied to commercial belt samples randomly selected from the market. As shown in FIG. 6A, the real-time testing result for the leather sample was pig leather with a confidence value of 100%. FIG. 6B shows that the real-time testing result of the belt sample was cattle leather. The confidence values for three repeated tests were 99.89%, 93.92%, and 99.77% respectively.

In the present invention, the mass spectrometric profiles of leathers from different animal origins can be reviewed and compared through Step 3. The main characteristic ions and corresponding relative contents in different animal leathers are shown in Table 3. In addition to real-time recognition and identification, these information enables manual check to confirm whether the real samples contain the characteristic ions corresponding to a certain category of animal leather and whether its mass spectrometric profiles comply with the characteristics of a certain category of animal leather. Moreover, since there is much difference in the mass spectra between synthetic leather and natural leather, they can be distinguished by checking the distinct mass spectral characteristics. Based on Step 4, the important ions (VIP>1, analysis of variance p-value<0.05, and max fold change>2) during model establishment can be found accurately. Corresponding compounds can be tentatively identified as the characteristic components in different animal leathers based on their accurate mass and isotopic ratio by searching relevant database.

The foregoing embodiments are merely illustrative of preferred embodiments of the present invention and are not intended to limit the scope of the present invention. Various variations and modifications made to the technical solutions of the present invention by those skilled in the art without departing from the spirit of the present invention are embraced in the protection scope of the present invention as defined by the appended claims.

What is claimed is:

1. A method for authentication of animal species origin of leather products, which includes the following steps:
    step 1, model establishment:
    (1) collecting leather samples from different animal species origins, set mass spectrometric parameters, cutting the grain surface of leather samples using a preheated electric soldering iron, instantly producing a stream of aerosols containing a large amount of complex ion mixtures, and detecting the resulting sample ions using the mass spectrometer;
    (2) importing the REIMS data into a LiveID software, creating a multivariate statistical model based on PCA-LDA analysis of the REIMS data, and evaluating the model with cross-validation tests;
    step 2, analysis of real leather samples:
    opening the LiveID software, selecting the established model, loading the same mass spectrometric parameters as in step 1, cutting the surface of real leather samples using the preheated electric soldering iron, producing real-time detection results for sample analysis;
    wherein the model of the electric soldering iron was CS-20 with a voltage of 220 V, a temperature of 380° C., and a full length of 170 mm;
    wherein the mass spectrometer was a QTOF high-resolution mass spectrometer equipped with a REIMS ambient ionization source; a scan time was 1 s; the mass spectra were acquired over the m/z 50-1200; a data acquisition could be carried out in either positive or negative ion mode;
    wherein the mass spectrometric parameters are as follows: cone voltage of 40 V, heater bias voltage of 60 V, cutting length of 1 cm, and auxiliary solvent flow rate of 0.15 mL/min.

2. The method for authentication of animal species origin of leather products of claim 1, wherein a stream of aerosols containing a large amount of complex ion mixtures were produced during the process of cutting leather samples; an orthogonal nitrogen-driven Venturi pump at 2 bar transported to the resulting aerosols through a PTFE tube to a REIMS atmospheric interface chamber, where the aerosols collided with a heated helical coil set at the parameters of 4.5 A, 4.2 V, and 800° C.;
    afterwards, the ions from leather samples were subjected to mass spectrometric analysis; for impurity elution, signal enhancement, and lock-mass correction, an auxiliary solution of leucine enkephalin in isopropanol at a concentration of 0.2 ng/μL was continuously infused into the REIMS source using a syringe pump; mass drift was corrected based on reference peaks at m/z 554.2615 in the negative ion mode and m/z 556.2771 in the negative ion mode corresponding to the deprotonated or protonated leucine enkephalin.

3. The method for authentication of animal species origin of leather products of claim 1, wherein there was step (A) between step 1 and step 2: reviewing the REIMS spectra of leather samples using a MassLynx software and examine the distribution of characteristic ions varied from leather to leather and the interspecies differences of ion responses among various leather samples.

4. The method for authentication of animal species origin of leather products of claim 3, wherein there was step (B) after step (A): further analyzing the REIMS data using a Progenesis QI software, wherein:
  (a) peak alignment: a REIMS raw data from all the leather samples were imported into the Progenesis QI software, where the ion peaks were automatically aligned for correct comparison of compounds in different leather samples;
  (b) grouping: all the data were grouped based on animal leather categories;
  (c) peak extraction: the peaks in the raw data were detected for discovering the compounds in leather samples;
  (d) deconvolution: after peak extraction, the ions in different adduct forms for the same compound in leather samples were grouped, calculating the neutral mass of the compound based on the mass difference between various adduct forms; when VIP score of a compound was greater than 1, the result validity for the compound was reviewed by deconvolution; select the compound in the left list, and then check the result using a visualized graph in the rest part of a screen; first, use deconvolution matrix to find any apparent problems; if there was uncertainty for an ion, check whether its mass spectrum matched other ions of the compound;
  (e) compound identification: identify the compounds that may possibly exist in various animal leathers with the following procedure: select identification method of Progenesis MetaScope; select the search parameter of Tutorial No Fragmentation; select the compound database of Basic lipids; set the mass accuracy of <5 ppm and the retention time deviation within 0.1 min;
  (f) compound identification results review: check all the identified compounds in animal leathers with VIP scores above 1 in detail;
  (g) comprehensive statistical analysis: PCA uses the compound abundance level to find a principal axis for abundance changes, transforming and plotting the abundance data in a principal component space; the PLS-DA model was established by separating the running samples according to the abundance changes; the data from the same animal origin were clustered into the same region, while the data from different animal origins featured complete spatial separation;
  based on grouping conditions, the interspecies differences between individual animal leather categories were analyzed; a VIP-variable importance plot for the multivariate statistical analysis displayed the relative influence of each ion on all responses in decreasing VIP score order from the most influential to the least influential; as to a VIP versus PLS coefficients, important x variable had higher positive VIP scores and greater positive or negative coefficient values, revealing the prominent marker compounds that highly contributed to the discriminant separation model between leather species;
  (h) find out potential marker compounds for each leather sample and determine the relative content of the main compounds.

5. The method for authentication of animal species origin of leather products of claim 1, wherein there was step 3 after step 2: SEM was used to characterize muscle face fibers and cross sections of leather samples; or if a real-time recognition result using the REIMS method was negative, it indicated that the sample did not belong to any animal leather category investigated in the model; for instance, for a split cattle leather sample, the grain surface layer consisted of synthetic materials and a muscle surface layer consisted of dermal fibers; SEM could be used to observe microstructures of the muscle surface layer of the leather sample to determine whether the muscle surface layer consisted of natural leather fibers; the characterization method included the following steps: a small number of fibers from the muscle surface layer of the leather sample was adhered to a conductive adhesive of a sample plate using a tweezer, then gold sputtered for 160 s; the microstructures of the leather fibers were characterized using SEM operated at a working voltage of 15.0 kV, a magnification of 60000-80000 times, and a working distance of 12200 µm.

* * * * *